(12) United States Patent
Smith et al.

(10) Patent No.: US 11,964,045 B2
(45) Date of Patent: Apr. 23, 2024

(54) NATURAL SKIN PENETRATING MOISTURIZER FORMULATIONS

(71) Applicant: DAMIVA, INC., Toronto (CA)

(72) Inventors: Gardiner F H Smith, Elizabeth, WV (US); Chia Chia Sun, Toronto (CA)

(73) Assignee: DVA INC., Vaughan (CA)

( * ) Notice: Subject to any disclaimer, the term of this patent is extended or adjusted under 35 U.S.C. 154(b) by 0 days.

(21) Appl. No.: 17/903,598

(22) Filed: Sep. 6, 2022

(65) Prior Publication Data

US 2023/0124139 A1 Apr. 20, 2023

Related U.S. Application Data

(63) Continuation of application No. 17/046,685, filed as application No. PCT/IB2019/052972 on Apr. 10, 2019, now Pat. No. 11,446,232.

(60) Provisional application No. 62/655,566, filed on Apr. 10, 2018.

(51) Int. Cl.
| | | |
|---|---|---|
| A61K 36/00 | (2006.01) | |
| A61K 8/34 | (2006.01) | |
| A61K 8/36 | (2006.01) | |
| A61K 8/37 | (2006.01) | |
| A61K 8/49 | (2006.01) | |
| A61K 8/67 | (2006.01) | |
| A61K 8/73 | (2006.01) | |
| A61K 8/92 | (2006.01) | |
| A61K 8/9789 | (2017.01) | |
| A61Q 19/00 | (2006.01) | |

(52) U.S. Cl.
CPC ............ *A61K 8/922* (2013.01); *A61K 8/347* (2013.01); *A61K 8/36* (2013.01); *A61K 8/37* (2013.01); *A61K 8/492* (2013.01); *A61K 8/498* (2013.01); *A61K 8/67* (2013.01); *A61K 8/735* (2013.01); *A61K 8/9789* (2017.08); *A61Q 19/007* (2013.01); *A61K 2800/5922* (2013.01)

(58) Field of Classification Search
CPC .................................................. A61Q 19/007
See application file for complete search history.

(56) References Cited

U.S. PATENT DOCUMENTS

2016/0346339 A1 12/2016 Finley et al.
2018/0049971 A1* 2/2018 Druilhet ................. A61K 8/678

FOREIGN PATENT DOCUMENTS

CA 2925468 A1 4/2015

OTHER PUBLICATIONS

Athar et al., "Taxonomic perspective of plant species yielding vegetable oils used in cosmetics and skin care products," African Journal of Biotechnology, 2005, vol. 4, No. 1, pp. 36-44 [online] (whole document, specifically Table 1) [retrieved on May 29, 2019], Retrieved from the Internet: https://pdfs.semanticscholar.org/1692/11b8b6f8e30f7flc6a32536644b311386c25.pdf?_ga=2.113043020.932938199.1559141791-154035446.1559141791.

Brown et al., "Hyaluronic acid: a unique topical vehicle for the localized delivery of drugs to the skin," Journal of the European Academy of Dermatology and Venereology, 2005, vol. 19, No. 3, pp. 308-318, [online] (whole document) [retrieved on May 29, 2019]. Retrieved from the Internet: http://statis.beautyguideblog.com/hyaluronic.pdf.

International Search Report dated Jun. 5, 2019 in corresponding International Application No. PCT/IB2019/052972.

Written Opinion dated Jun. 5, 2019 in corresponding International Application No. PCT/IB2019/052972.

* cited by examiner

*Primary Examiner* — Qiuwen Mi

(74) *Attorney, Agent, or Firm* — Venable LLP; Keith G. Haddaway; Brenden G. McDearmon

(57) ABSTRACT

The invention relates to a personal care product for alleviating skin dryness, including facial skin dryness, body dryness, and breast skin dryness and for use as a massage oil. Embodiments of the personal care product include a formulation including cocoa butter, kokum butter, shea olein, and hyaluronic acid and/or cannabis oil. The personal care product may also include other plant-based glycerides, natural hormones, herbal roots and oils, amino acids, dietary supplements. The personal care product is substantially free of added water, alcohol, synthetic chemical, anti-microbial, and synthetic hormone.

19 Claims, No Drawings

NATURAL SKIN PENETRATING MOISTURIZER FORMULATIONS

This application is a continuation of U.S. application Ser. No. 17/046,685, filed Oct. 9, 2020, now U.S. Pat. No. 11,446,232, issued on Sep. 20, 2022, which is a U.S. National Stage Application under 35 U.S.C. § 371 on International Application No. PCT/IB 2019/052972, filed Apr. 10, 2019, which claims priority benefit from U.S. Provisional Patent Application No. 62/655,566, filed on Apr. 10, 2018, the entire content of which is incorporated herein by reference. All references cited anywhere in this specification, including the Background and Detailed Description sections, are incorporated by reference as if each had been individually incorporated.

FIELD OF THE INVENTION

This invention relates to personal care products. More specifically, this invention relates to all natural personal care products for use by women or men. The personal care products include moisturizers for the face and body. The personal care products also include massage oil and body serums.

BACKGROUND

The human body constantly reacts and adjusts to environmental impacts that can come from many sources. For example, studies have shown that volatile organic compounds (VOCs) released into the atmosphere from paints, pesticides, perfumes, household cleaners are inhaled into the body and absorbed through the skin. These can have adverse effects on the skin and in the body. In addition to VOCs, other chemicals such as butylhydroxytoluene, perfluorooctanoic acid, and tributylin are ingested into the body though consumption of prepackaged food. Studies have shown that some of these chemicals cause weight gain and disrupt human hormones.

Women's bodies in particular undergo myriad changes through time, from puberty to childbearing years to postmenopause. A common problem occurring due to change of hormone is tissue dryness. This dryness can occur in skin on any part of the body, for example the breasts and the face. Breast dryness or tenderness, also known as mastalgia, can result in discomfort in normal daily activities, including disruption of normal movement, concentration, sleep, and intimacy. There is, thus, a continuing need for products that address biological changes of women that occur before, during and after childbearing period on to post-menopause.

To alleviate dryness, particularly when associated with hormonal changes, women have been prescribed low-dose birth control pills to address the change of hormones in their bodies. Others have also used birth control skin patches, vaginal rings, and progesterone injections as hormone treatments. While these therapies may alleviate some related symptoms due to change of hormones in the body, such as hot flashes, sweats, and mood changes, they are less effective in treating dryness, such as skin dryness, breast dryness, vaginal dryness, and vulval dryness, and the concomitant results of dryness, such as skin discomfort, breast sensitization, vaginal pain, and discomfort during sex. Women have also used personal lubricants, body lotions, and petroleum jelly-based products to ease some of these discomforts. Others use prescription hormone drug treatments to introduce synthetic chemical substitutes into the body for the loss of natural hormones during perimenopause.

Unfortunately, most personal care products on the market are water-based, oil-based, or silicone-based and are prone to contamination unless they contain synthetic chemicals such as preservatives, anti-microbial agents and stabilizers. Addition of these components is undesirable.

Therefore, there is a need for products that specifically target dryness, in particular dryness in sensitive areas for women who are experiencing hormonal changes. More importantly, an all-natural product is advantageous for the skin to retain moisture. Products are needed to alleviate facial and breast dryness and can regulate the sleep cycle for women experiencing perimenopause. Moreover, men and children may also benefit from these all natural products that are free of artificial synthetic chemicals.

DESCRIPTION OF EMBODIMENTS OF THE INVENTION

The present invention relates to a personal care product. In general, the personal care product promotes healthy skin, especially skin in sensitive areas such as the vaginal track, genitourinary tissue, breasts and face. In embodiments, the products are used for alleviating skin dryness. In particular, the personal care product of the present invention is an all-natural product devoid of any artificial synthetic chemicals, alcohol, water, or synthetic hormones. These artificial synthetic chemicals not naturally occurring or found in nature. Embodiments of the invention include a base material, as defined further below, together with hyaluronic acid or a cannabis oil. Exemplary embodiments of the present invention include cocoa butter, kokum butter, shea olein, and hyaluronic acid and/or a cannabis oil. The personal care product may also include other plant-based glycerides, natural hormones, herbal roots and oils, amino acids, vitamins, minerals, and other dietary supplements as part of the base material. In embodiments, the personal care product is substantially free of added water, alcohol, synthetic chemical, anti-microbial agents, preservatives and synthetic hormones. The invention utilizes natural substances that replenish dry skin when applied on the skin.

The invention may also be formulated as massage oils or serums. When formulated as such, the personal care product may be modified to contain more oils than butters to provide a more liquid consistency.

As used herein, the term "formulation" refers to the prepared personal care product and the terms "formulation" and "personal care product" are generally used interchangeably.

All percentages refer to weight percent (wt. %) of the component in the final product, i.e. the weight of the component as compared to the total product weight. Weight percentages are subject to precision and rounding and thus, in general, there is some variability in exact measures of weight percent, as would be readily recognized by persons skilled in the art.

As used herein, "plant glycerides" or "plant-based glycerides" refers to a plant extract of fatty acid glycerides that may include monoglycerides, diglycerides and triglycerides. In diglycerides and triglycerides, the fatty acids may be the same or different. Typical plant glycerides contain a mixture of glycerides with different fatty acids. However, the composition of glycerides from a particular plant extracted in a particular way provides a relatively consistent fatty acid content. Specific plant glycerides from various sources and in various forms are well known in the art.

Plant-based glycerides can mainly contain fatty acids such as palmitic acid, stearic acid, linoleic acid, linolenic acid, arachidic acid, oleic acid, and others, esterified onto glycerol to form the glycerides. The plant-based glycerides can be in the form of a butter (solid at room temperature), a paste (semi-solid or cream-like at room temperature), or an oil (liquid at room temperature). Their physical properties depend on the specific composition of the glycerides. Non-limiting examples of plant-based glycerides include extracts of shea, cocoa, kokum, mango, palm, sunflower, walnut, avocado, hemp, and almond, many of which may be in the form of a butter, paste or oil. These products are known and have their generally meaning as understood in the art. In some embodiments, the plant-based glycerides are deodorized.

Different plant glycerides contain different amount of monoglycerides, diglycerides and triglycerides. Depending on the specific plant glycerides that are used, the concentration of the plant butters and oils must be adjusted so that the viscosity of the final product is optimized to achieve desirable outcome. Moreover, temperature of use also plays a role in the selection and concentration of each plant glyceride. For example, typical commercial products use chemical stabilizers in the cream or lotion to maintain viscosity consistency in varying temperatures. In comparison, the present invention is substantially free of chemical stabilizers and care must be used to achieve the desirable viscosity for the product. Viscosity can be adjusted by varying the amount of different plant glycerides, including butters, oils, and powders. Typically, lotions are pourable with a viscosity of <30,000 cp (at 5 rpm and 25° C.). In comparison, creams may have higher viscosity.

In embodiments, the personal care products of the invention are in the form of a lotion or cream. Exemplary embodiments are lotions with a viscosity suitable for application by a manual pump device. Persons skilled in the art are well aware of such devices and can easily assess the viscosity needed for this type of application. While the personal care products of the invention contain sufficient butter-type plant glycerides to maintain a cream-like texture and feel upon application, the use of increased amounts and particular novel combination of plant glycerides reduces overall viscosity to allow suitable dispensing from a manual pump type container at different temperatures, for example from between about 45° F. to about 100° F.

As will be appreciated, because the personal care product of the invention is non-aqueous, it does not have a readily quantifiable pH. Accordingly, references to pH in the present specification refer to the pH of the product in an aqueous environment. Because the skin contains some water, the pH described can be considered the pH obtained when the personal care product of the invention is applied to the skin or tissue.

As used herein, the term "hyaluronic acid" refers not only to the acid, but also to salts such as sodium hyaluronate, and the terms are used interchangeably. Unless specified otherwise, sodium hyaluronate can be can be replaced with other hyaluronic acid salts such as potassium hyaluronate and the like. In general, hyaluronic acid and hyaluronate salts can be used interchangeably in products and formulations of the invention, unless stated otherwise. Persons skilled in the art will be able to identify appropriate forms of hyaluronic acid. Hyaluronic acid is a naturally occurring substance found in various connective tissue in the human body. The hyaluronic acid used in the present invention can be obtained from a natural source or a synthetic bioidentical hyaluronic acid that is indistinguishable from naturally occurring hyaluronic acid.

As used herein and unless otherwise clear from context, the term "cannabis oil" generally refers to a hemp extract containing one or more cannabinoids, as identified herein, or cannabinoids that may be obtained from a hemp extract. The cannabis oil may contain a particular cannabinoid compound, a class of cannabinoid structurally related compounds, or a range of cannabinoid compounds. As such, a cannabis oil may comprise a single compound or a mixture of compounds. Cannabis oil can also be a mixture of cannabinoids from any source. Cannabinoids used in the present invention can be obtained from a natural source or can be a synthetic bioidentical cannabinoid that is indistinguishable from a naturally occurring cannabinoid.

According to the invention, the personal care product can be in the form of a cream or lotion. For example, embodiments of the invention include a nursing cream or lotion, a facial cream or lotion, a night cream or lotion, a breast cream or lotion, a body cream or lotion, a facial serum or lotion, or a massage oil for the body.

An embodiment of the invention relates to a personal care product that may include plant-based glycerides, such as cocoa butter, kokum butter, and shea olein. Embodiments also include hyaluronic acid, and/or a cannabis oil. Some embodiments of the invention further comprise other plant-based glycerides, such as those containing oleic acid. Oleic acid glycerides can be found in olive oil, pecan oil, canola oil, peanut oil, macadamia oil, sunflower oil, grape seed oil, sea buckthorn oil, sesame oil, poppyseed oil, and other plants or seeds oil. In an embodiment sunflower oil is a source of oleic acid glycerides. In exemplary embodiments, the sunflower oil can contain 30% mono-unsaturated fatty acids, including as oleic acid, 60% polyunsaturated fatty acids, and 10% saturated fatty acids.

Embodiments of the invention include plant triglycerides as a base material. For example, in embodiments of the invention the base material may include cocoa butter, kokum butter, shea olein, and, optionally, oleic acid, hemp oil, borage oil and/or argan oil. The selection and amounts of plant based glycerides can be varied to achieve desired physical properties. The identity and quantities of materials described herein give particularly desirable physical characteristics.

In an exemplary embodiment, the base material may include about 1 wt. % to about 10 wt. % cocoa butter, about 0.1 wt. % to about 10 wt. % kokum butter, and about 6 wt. % to about 15 wt. % shea olein, in which percentages are expressed as a part of the entire material. Particular embodiments of the invention may have modified amounts of these materials. For example, some embodiments contain about 3 wt. % to about 10 wt. % cocoa butter, about 3 wt. % to about 10 wt. % kokum butter, and about 6 wt. % to about 15 wt. % shea olein. Other embodiments contain about 5 wt. % to about 8 wt. % cocoa butter, about 3 wt. % to about 5 wt. % kokum butter, and about 10 wt. % to about 14 wt. % shea olein. Still other exemplary embodiments contain about 1 wt. % to about 7 wt. % cocoa butter, about 0.1 wt. % to about 5 wt. % kokum butter, and about 6 wt. % to about 15 wt. % shea olein. Some exemplary embodiments include about 2 wt. % to about 5 wt. % cocoa butter, about 0.5 wt. % to about 3 wt. % kokum butter, and about 7 wt. % to about 11 wt. % shea olein.

Embodiments of the invention may include other plant based glycerides and oils such as one or more of an oleic acid glyceride, argan oil, hemp oil or borage oil. Some embodiments of the invention contain about 30 wt. % to about 40 wt. %, for example about 33 wt. % to about 38 wt. %, oleic acid glyceride, about 25 wt. % to about 35 wt. %, for example, about 28 wt. % to about 33 wt. %, hemp oil and about 3 wt. % to about 10 wt., for example, about 4 wt. % to about 7 wt. %, borage oil. In embodiments of the invention containing argan oil, it may be present in an amount of from about 0.5 wt. % to about 5 wt. %, or from about 9 wt. % to about 15 wt. %. Particular embodiments contain from about 1 wt. % to about 3 wt. %, or from about 10 wt. % to about 15 wt. % argan oil.

Embodiments of the invention may include oleic acid, argan oil, and magnesium. Embodiments of the invention may further include hemp oil and borage oil. Embodiments of the invention may further include Vitamin D3 and chamomile oil. Embodiments of the invention may further include valerian root oil and lavender oil. Embodiments of the invention may further include melatonin and sodium cocoate. Embodiments of the invention may further include glucosamine, kojic acid, jasmine oil, and lemongrass oil. Embodiments of the invention may further include spilanthes, chasteberry, dong quai, maca, and black cohash. Embodiments of the invention may further include nobileton, quercetin, and patchouli. Embodiments of the invention may further include sucrose, spilanthes, and chasteberry.

For example, embodiments of the invention may include one or more ingredients from about 3 wt. % to about 10 wt. % cocoa butter, from about 3 wt. % to about 10 wt. % kokum butter, from about 6 wt. % to about 15 wt. % shea olein, and from about 30 wt. % to about 40 wt. % oleic acid. Other embodiments of the invention may include one or more ingredients from about 0.2 wt. % to about 3 wt. % vitamin E, from about 0.5 wt. % to about 5 wt. % argan oil, and from about 0.01 wt. % to about 2 wt. % magnesium. Any of the embodiments disclosed herein can also contain, from about 25 wt. % to about 35 wt. % hemp oil, and from about 3 wt. % to about 10 wt. % borage oil. Any of the embodiments disclosed herein can also contain one or more ingredients from about 0.01 wt. % to 2 wt. % Vitamin D3, from about 0.01 wt. % to about 2 wt. % chamomile oil, from about 0.01 wt. % to about 2 wt. % valerian root, from about 0.01 wt. % to about 2 wt. % lavender (oil). Any of the embodiments disclosed herein can also contain one or more of from about 0.05 wt. % to about 4 wt. % melatonin, from about 0.5 wt. % to about 6 wt. % sodium cocoate, from about 0.05 wt. % to about 4 wt. % glucosomine, from about 0.01 wt. % to about 2 wt. % kojic acid, from about 0.01 wt. % to about 2 wt. % jasmine oil, from about 0.01 wt. % to about 2 wt. % lemongrass oil, from about 0.01 wt. % to about 2 wt. % gingko, from about 0.05 wt. % to about 4 wt. % spilanthes, from about 0.01 wt. % to about 2 wt. % chasteberry, from about 0.01 wt. % to about 2 wt. % dong quai, from about 0.01 wt. % to about 2 wt. % maca, from about 0.01 wt. % to about 2 wt. % black cohash, from about 0.005 wt. % to about 1 wt. % nobiletin, from about 0.01 wt. % to about 2 wt. % quercetin, and from about 0.01 wt. % to about 2 wt. % pathouli.

The remainder of the base material may include one or more of oleic acid glycerides, argan oil, hemp oil, and borage oil. The base material may be formulated so that the final formulation contains these components in the following amounts: Oleic acid glycerides may be present in an amount of from about 30 wt. % to about 40 wt. %; for example, from about 33 wt. % to about 37 wt. %. Argan oil may be present in an amount of from about 0.5 wt. % to about 5 wt. %; for example, from about 1 wt. % to about 3 wt. %. Hemp oil may be present in an amount of from about 25 wt. % to about 35 wt. %; for example, from about 28 wt. % to about 33 wt. %. Borage oil may be present in an amount of from about 3 wt. % to about 10 wt. %; for example, from about 4 wt. % to about 7 wt. %.

The base material may further include additional ingredients including fragrances, mineral, vitamins, penetration enhancers, and herbs. Examples of additional ingredients include Magnesium, Vitamin D3, chamomile oil, valerian root, lavender, melatonin, sodium cocoate, Vitamin E, spilantes, chasteberry, dong quai, maca, and black cohash. The base material may be formulated so that the final formulation contains these components in the following amounts: Magnesium may be present in an amount of from about 0.01 wt. % to about 2 wt. %; for example, from about 0.5 wt. % to about 1 wt. %. Vitamin D3 may be present in an amount of from about 0.01 wt. % to about 2 wt. %; for example, from about 0.5 wt. % to about 1 wt. %. Chamomile oil may be present in an amount of from about 0.01 wt. % to about 2 wt. %; for example, from about 0.5 wt. % to about 1 wt. %. Valerian root may be present in an amount of from about 0.01 wt. % to about 2 wt. %; for example, from about 0.5 wt. % to about 1 wt. %. Lavender may be present in an amount of from about 0.01 wt. % to about 2 wt. %; for example, from about 0.5 wt. % to about 1 wt. %. Melatonin may be present in an amount of from about 0.05 wt. % to about 4 wt. %; for example, from about 0.1 wt. % to about 2 wt. %. Sodium cocoate may be present in an amount of from about 0.5 wt. % to about 6 wt. %; for example, from about 1 wt. % to about 4 wt. %. Vitamin E may be present in an amount of from about 0.2 wt. % to about 3 wt. %; for example, from about 0.5 wt % to about 1.5 wt. %. Spilantes may be present in an amount of from about 0.01 wt. % to about 4 wt. %; for example, from about 0.5 wt. % to about 3 wt. %. Chasteberry may be present in an amount of from about 0.01 wt. % to about 2 wt. %; for example, from about 0.5 wt. % to about 1 wt. %. Dong quai may be present in an amount of from about 0.01 wt. % to about 2 wt. %; for example, from about 0.5 wt. % to about 1 wt. %. Maca may be present in an amount of from about 0.01 wt. % to about 2 wt. %; for example, from about 0.5 wt. % to about 1 wt. %. Black cohash may be present in an amount of from about 0.01 wt. % to about 2 wt. %; for example, from about 0.5 wt. % to about 1 wt. %.

In an embodiment, the base material for transdermal application may include natural ingredients, such as, for example, about 3 wt. % cocoa butter, about 1.5 wt. % kokum butter, about 9 wt. % shea olein, about 1 wt. % vitamin E, about 34 wt. % oleic acid (30% mono, 60% poly/sunflower), about 14.4 wt. % argan oil, about 0.1 wt. % magnesium, about 29.5 wt. % hemp oil, about 6 wt. % borage oil, and about 1.5 wt. % sucrose cocoate.

In addition to the base material, embodiments of the invention include hyaluronic acid or a cannabis oil.

Hyaluronic acid is a skin hydrating agent that can help restore water to dehydrated skin. When applied according to a method of the invention, hyaluronic acid molecules can deliver substantially instant hydration to the skin.

The hyaluronic acid used in the invention generally has a very low molecular weight, e.g. about 100 kDa or less, about 50 kDa or less, or about 5 kDa. This low molecular weight allows for increased permeation through the skin compared to high molecular weight hyaluronic acid. The hyaluronic acid can rejuvenate the skin by improving its viscoelastic properties and significantly decreases deep wrinkles. Hyaluronic acid is commercially available from a number of sources. Embodiments of the invention include 0.0001 wt. % to 2 wt. % hyaluronic acid, 0.01 wt. % to 2 wt. % hyaluronic acid, 0.0001 wt. % to 1 wt. % hyaluronic acid, 0.005 wt. % to 0.5 wt. % hyaluronic acid, or 0.05 wt. % to 0.15 wt. % hyaluronic acid. Some embodiments of the invention include 0.05 wt. % to 0.15 wt. % hyaluronic acid.

Embodiments of the invention may include cannabis oil. Cannabis oil includes one or more compounds from a vast array cannabinoids, mostly isolated from (or synthetic compounds identical to compounds isolated from) cannabis and other plants. Cannabinoids have been the subject of a great deal of recent research and have many benefits on physical and mental health. Cannabinoids used in the invention include a broad spectrum hemp extract that includes a mixture of cannabinoids. Alternatively, one or more cannabinoid compounds can be individually isolated or synthesized for use in the composition.

Cannabis Oil, or broad spectrum hemp extract, is a cannabis extract containing one or more cannabinoids. Exemplary cannabinoids include THCA (Tetrahydrocannabinolic acid), CBD (Cannabidiol), CBDA (Cannabidiolic Acid), CBN (Cannabinol), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), CBE (Cannabielsoin), and CBT (Cannabicitran). In exemplary embodiments, the cannabis oil (or cannabinoids contained therein) are decarboxylated. The cannabis oil may also contain THC (Tetrahydrocannabinol). In some embodiments, the THC may be present in about 1-3 wt. % in addition to the cannabis oil of the product. In other embodiments, the THC may be present in about 0 wt. % to about 0.25 wt. % of the formulation. The cannabis oil may contain, for example, between about 10 wt. % and 75 wt. % of the one or more cannabinoids. Exemplary embodiments contain about 10-50 wt. % of each cannabinoid in the oil. Exemplary formulations that do not include THC (either added separately from the cannabis oil or as a component of the cannabis oil) can comprise 2-5 cannabinoids. In these exemplary embodiments, at least 65 wt. % of the cannabinoid content comprises decarboxylated CBD.

In some embodiments, the products of the present invention may include the cannabis oil (also at times referred to as hemp extract) in an about of between 0.01 wt. % to 2 wt. %, for example, about 0.05 wt. % to about 1 wt. %. In some embodiments, the cannabis oil may exclude THC. If included, the THC in an amount of less than 5 wt. %, less than 3 wt. % or less than 1.5 wt. %. In an embodiment, the broad spectrum hemp extract without THC may include 2 to 10, 2 to 6, or 2 to 5 different cannabinoids in varying amounts. For example, the hemp extract may include two or more cannabinoids elected from CBDV, CBDA, CBGA, CBG, CBD, CBN, d9-THC, d8-THC, CBC, or THCA. In an embodiment, the hemp extract may include decarboxylated CBD in more than 50 wt. %, more than 55 wt. %, or more than 65 wt. %.

In some embodiments, the cannabis oil is refined so that it lacks any detectable cannabis odor. In some embodiments, the cannabis oil is refined so that it lacks any detectable cannabis terpenes. Extracts lacking cannabis odor and/or terpenes are particularly desirable for use in cosmetic products, for example in facial creams.

Embodiments of the invention can include 0.0001 wt. % to 2 wt. % cannabinoid, 0.01 wt. % to 2 wt. % cannabinoid, 0.01 wt. % to 0.05 wt. % cannabinoid, 0.005 wt. % to 0.5 wt. % cannabinoid, or 0.05 wt. % to 0.25 wt. % cannabinoid. Some embodiments of the invention include 0.05 wt. % to 0.25 wt. % cannabinoid. In exemplary embodiments, the *cannabis* oil is a broad spectrum hemp extract. In other exemplary embodiments, the *cannabis* oil is cannabidiol.

In some embodiments, the products of the present invention may include hemp oil. Hemp oil is obtained by pressing hemp seeds and is of high nutritional value because of its 3:1 ratio of omega-6 to omega-3 essential fatty acids. Hemp oil is different from hemp extract (or cannabis oil), which is a partially purified mixture of cannabinoids from the hemp plant.

In an embodiment, a formulation for alleviating breast dryness may include natural ingredients, such as, about 6 wt. % cocoa butter, about 4.5 wt. % kokum butter, about 12 wt. % shea olein, about 1 wt. % vitamin E, about 0.1 wt. % hyaluronic acid, about 35 wt. % oleic acid, about 2 wt. % argan oil, about 0.1 wt. % magnesium, about 31.9 wt. % hemp oil, about 6 wt. % borage oil, about 1 wt. % spilanthes, about 0.1 wt. % chasteberry, about 0.1 wt. % dong quai, about 0.1 wt. % maca, and about 0.1 wt. % black cohash.

An embodiment of the invention includes about 6 wt. % cocoa butter, about 4.5 wt. % kokum butter, about 12 wt. % shea olein, about 1 wt. % vitamin E, about 0.1 wt. % hyaluronic acid, about 36 wt. % oleic acid, about 2 wt. % argan oil, about 0.1 wt. % magnesium, about 32 wt. % hemp oil, about 6 wt. % borage oil, about 0.1 wt. % Vitamin D3, about 0.1 wt. % chamomile oil, about 0.1 wt. % valerian root, and about 0.1 wt. % lavender.

In an embodiment, a massage oil formulation of the invention includes about 3 wt. % cocoa butter, about 1.5 wt. % kokum butter, about 9 wt. % shea olein, about 1 wt. % vitamin E, about 34 wt. % oleic acid (sunflower oil), about 14.2 wt. % argan oil, about 6 wt. % borage oil, about 29.4 wt. % hemp oil, about 1.6 wt. % sucrose cocoate, about 0.2 wt. % cannabis oil, and about 0.1 wt. % lemongrass extract.

In an embodiment, a formulation for alleviating sleep problems, which may be in the form of a facial cream, may include natural ingredients, such as, about 6 wt. % cocoa butter, about 4.3 wt. % kokum butter, about 12 wt. % shea olein, about 1 wt. % vitamin E, about 0.1 wt. % hyaluronic acid, about 34 wt. % oleic acid, about 2 wt. % argan oil, about 0.1 wt. % magnesium, about 30.6 wt. % hemp oil, about 6 wt. % borage oil, about 0.1 wt. % Vitamin D3, about 0.1 wt. % chamomile oil, about 0.1 wt. % valerian root, about 0.1 wt. % lavender, about 0.5 wt. % melatonin, and about 3 wt. % sodium cocoate.

In an embodiment, a formulation for facial treatment, which may be in the form of a facial serum, may include natural ingredients, such as, about 3 wt. % cocoa butter, about 1.6 wt. % kokum butter, about 9 wt. % shea olein, about 1 wt. % vitamin E, about 36 wt. % oleic acid (sunflower oil), about 11 wt. % argan oil, about 6 wt. % borage oil, about 30.1 wt. % hemp oil, about 0.1 wt. % hyaluronic acid, about 0.1 wt. % magnesium, about 0.1 wt. % chamomile oil, about 1.5 wt. % sodium cocoate, about 0.1 wt. % Vitamin D3, about 0.1 wt. % rose oil, about 0.1 wt. % ginko biloba extract, and about 0.2 wt. % cannabis oil.

In an embodiment, a formulation for facial treatment, which may be in the form of a facial serum, may include natural ingredients, such as, about 3 wt. % cocoa butter, about 1.6 wt. % kokum butter, about 9 wt. % shea olein, about 1 wt. % vitamin E, about 0.1 wt. % hyaluronic acid, about 34 wt. % oleic acid (sunflower oil), about 11 wt. % argan oil, about 6 wt. % borage oil, about 29.3 wt. % hemp oil, about 0.1 wt. % kojic acid, about 3 wt. % glucosamine, about 0.06 wt. % rose oil, about 1.5 wt. % sodium cocoate, about 0.2 wt. % cannabis oil (hemp extract), and about 0.2 wt. % lavender.

An embodiment of the invention includes about 6 wt. % cocoa butter, about 4.5 wt. % kokum butter, about 12 wt. % shea olein, about 1 wt. % vitamin E, about 0.1 wt. % hyaluronic acid, about 36 wt. % oleic acid, about 2 wt. % argan oil, about 0.1 wt. % magnesium, about 31 wt. % hemp oil, about 6 wt. % borage oil, about 1 wt. % Glucosomine, about 0.1 wt. % kojic acid, about 0.1 wt. % jasmine oil, and about 0.1 wt. % lemongrass oil.

An embodiment of the invention includes about 6 wt. % cocoa butter, about 4.5 wt. % kokum butter, about 12 wt. % shea olein, about 1 wt. % vitamin E, about 0.1 wt. % hyaluronic acid, about 35.98 wt. % oleic acid, about 2 wt. % argan oil, about 0.1 wt. % magnesium, about 32 wt. % hemp oil, about 6 wt. % borage oil, about 0.02 wt. % nobiletin, about 0.2 wt. % quercetin, and about 0.2 wt. % patchouli.

An embodiment of the invention includes about 4-8 wt. % cocoa butter, about 3-6 wt. % kokum butter, about 10-14 wt. % shea olein, about 0.1-3 wt. % vitamin E, about 0.05-2 wt. % hyaluronic acid, about 33-40 wt. % oleic acid, about 1-3 wt. % argan oil, about 0.05-2 wt. % magnesium, about 0.05-2 wt. % Vitamin D3, about 0.05-2 wt. % chamomile oil, about 0.05-2 wt. % sucrose, about 0.05-2 wt. % gingko, and about 0.05-2 wt. % spilanthes.

In any of the above embodiments, a cannabis oil may be used in place of or in addition to hyaluronic acid. In such embodiments, the use may differ from that described above, i.e. a similar formulation using a cannabis oil may have effects associated with the cannabinoid that are other than or in addition to use for breast dryness or sleep problems. For example, cannabis oil containing formulations may be used as a massage oil, for example to provide sexuality, a complexion evening enhancement, or a facial muscle relaxer.

Embodiments of the invention may include cocoa butter, an edible vegetable fact extracted from the cocoa bean. Cocoa butter has a cocoa flavor and aroma. Its melting point is just below human body temperature. Cocoa butter contains between 57-64 wt. % saturated fats and 36-43 wt. % unsaturated fats. Embodiments of the invention include about 1 wt. % to about 10 wt. % cocoa butter, about 1 wt. % to about 7 wt. % cocoa butter, about 5 wt. % to about 8 wt. % cocoa butter, or about 2 wt. % to about 5 wt. % cocoa butter.

Embodiments of the invention may include kokum butter. Kokum butter is extracted from the seeds of the kokum tree. Kokum butter contains up to 60-65 wt. % saturated fatty acid and is a solid in room temperature. Embodiments of the invention include about 0.1 wt. % to about 10 wt. % kokum butter, include about 1 wt. % to about 10 wt. % kokum butter, about 0.1 wt. % to about 5 wt. % kokum butter, 3 wt. % to about 5 wt. % kokum butter, or 0.5 wt. % to about 3 wt. % kokum butter.

Embodiments of the invention may include shea olein, also referred to at times as shea butter or shea oil. Shea olein is an off-white or ivory-colored natural glyceride extracted from the nuts of shea trees. Shea olein melts at body temperature and it is absorbed rapidly into the skin. In embodiments of the present invention containing shea olein, the personal care product has the consistency of a paste. Embodiments of the invention include about 6 wt. % to about 15 wt. % shea olein, about 10 wt. % to about 14 wt. % shea olein, or about 7 wt. % to about 11 wt. % shea olein.

Embodiments of the invention may include hemp oil. Hemp oil is obtained by pressing hemp seeds and is of high nutritional value because of its 3:1 ratio of omega-6 to omega-3 essential fatty acids. Embodiments of the invention can include 25 wt. % to about 35 wt. % hemp oil, or about 28 wt. % to about 33 wt. % hemp oil.

Embodiments of the invention may include borage oil. Borage oil is derived from the seeds of the Borago officinalis. Borage oil has one of the highest amount of γ-linolenic acid (GLA) of seed oils. Embodiments of the invention include 0 wt. % to about 10 wt. % borage oil, or about 3 wt. % to about 10 wt. % borage oil, or about 4 wt. % to about 7 wt. % borage oil.

Water and alcohols (including diols and polyols) are dehydrating to skin membranes due to the concentration gradient of salts and sugars in intracellular fluids. Embodiments of the invention relate to a personal care product that is substantially free of added water or alcohols, including diols and polyols. For example, substantially free can mean that the personal care product has less than about 5 wt. % of added water or alcohols, less than about 4 wt. % of added water or alcohols, less than about 3 wt. % of added water or alcohols, less than about 2 wt. % of added water or alcohols, less than about 1 wt. % added water or alcohols, less than about 0.5 wt. % added water or alcohols, less than about 0.1 wt. % added water or alcohols, or less than about 0.05 wt. % added water or alcohols. For example, the personal care product is substantially free of methanol, ethanol, propanol, and other monohydric alcohols; ethylene glycol, propylene glycol, and other diols; and glycerol (glycerin), and other polyols. In exemplary embodiments, the personal care product contains no added water or alcohols.

Embodiments of the invention relate to personal care products that are substantially free of synthetic chemicals, such as synthetic preservatives, anti-microbial agents, or chemical stabilizers. Examples of synthetic preservatives, antimicrobial agents, and chemical stabilizers include benzoates (e.g., benzoic acid and sodium benzoate), hydroxybenzoate and derivatives, sorbates (e.g., sorbic acid and sodium sorbate), proprinates, nitrates, nitrite, sulfites (sulfur dioxide, sodium bisulfite), chelating agents, propyl gallate, gallic acid, sodium gallate, methyl paraben, propyl paraben, butyl paraben, ethyl paraben, quaternium-15, formaldehyde, lactic acid, propionic acid, sodium propionate, ascorbic acid, sodium ascorbate, butylated hydroxytoluene, butylated hydroxyanisole, tricolsan, phthalates, endocrine disrupting chemicals (e.g., bisphenol A, dichlorodiphenyltrichloroethane, polychlorinated biphenyls, polybrominated diphenyl ether, phthalates, perfluorooctanoic acid, polychlorinated dibenzo-dioxins, polychlorinated dibenzo-furans, polycyclic aromatic hydrocarbons, endosulfan, kepone, atrazine, vinclozolin) and tocopherols.

Substantially free of added synthetic chemicals can mean that the personal care product has less than about 5 wt. % of added synthetic chemicals, less than about 4 wt. % added synthetic chemicals, less than about 3 wt. % added synthetic chemicals, less than about 2 wt. % of added synthetic chemicals, less than about 1 wt. % added synthetic chemicals, less than about 0.5 wt. % added synthetic chemicals, less than about 0.1 wt. % added synthetic chemicals, or less than about 0.05 wt. % added synthetic chemicals. For example, substantially free can mean that the personal care product has less than about 5 wt. % of added synthetic anti-microbial agents, less than about 4 wt. % added synthetic anti-microbial agents, less than about 3 wt. % added synthetic anti-microbial agents, less than about 2 wt. % of added synthetic anti-microbial agents, less than about 1 wt. % added synthetic anti-microbial agents, less than about 0.5 wt. % added synthetic anti-microbial agents, less than about 0.1 wt. % added synthetic anti-microbial agents, or less than about 0.05 wt. % added synthetic anti-microbial agents. For example, substantially free can mean that the personal care product has less than about 5 wt. % of added chemical stabilizers, less than about 4 wt. % added chemical stabilizers, less than about 3 wt. % added chemical stabilizers, less than about 2 wt. % of added chemical stabilizers, less than about 1 wt. % added chemical stabilizers, less than about 0.5 wt. % added chemical stabilizers, less than about 0.1 wt. % added chemical stabilizers, or less than about 0.05 wt. % added chemical stabilizers. In exemplary embodiments, the personal care product contains no added synthetic chemicals, such as synthetic preservatives, anti-microbial agents, or chemical stabilizers.

Embodiments of the invention include a personal care product that may include melatonin. Melatonin is a hormone secreted in the brain that regulates sleep. Throughout perimenopause and menopause, melatonin production declines, making sleep more difficult. Furthermore, cortisol production periodically spikes upward, causing wakefulness. Melatonin provides the advantage of treating sleep-wake cycle disorders and can be used to treat insomnia. Humans have melatonin receptors on their skin and therefore can absorb melatonin topically to regulate sleep cycle and to alleviate insomnia.

Embodiments of the invention that include melatonin may also include a natural transdermal carrier, which can assist in distributing the melatonin across the skin systemically. In an embodiment, argan oil, oleic acid and sucrose cocoate may be used as natural transdermal carrier. Other natural transdermal carriers may also be use, an example of transdermal carrier is Spilanthes. Spilanthes is a plant extract from *Spilanthes acmella*. Spilanthes can be used as a penetration enhancer to aid the transdermal delivery of natural ingredients. Other naturally derived transdermal carriers such as peppermint extract, eucalyptus oil, niaouli oils and others may be used. Oral melatonin supplements have the disadvantage that melatonin is metabolized within an hour. Therefore, if taken prior to going to sleep and the melatonin is not taken in sufficient quantity, the oral melatonin may not provide sufficient assistance with sleep. In comparison, a dermal or topical application of melatonin according to formulations of the present invention can distribute systemically throughout the course of the night, thereby maintaining efficacious serum levels to aid sleeping.

Embodiments of the invention may include 0.01 wt. % to 2 wt. % melatonin, 0.05 wt. % to 1 wt. % melatonin, or 0.1 wt. % to 1 wt. % melatonin. Embodiments of the invention may include 0.5 wt. % melatonin, 500 mg melatonin/mL composition (i.e., about 0.5 wt. %), 200 mg melatonin/mL composition (i.e., about 0.02 wt. %), or 100 mg melatonin/mL composition (i.e., about 0.1 wt. %). Melatonin may be a powder. Embodiments of the invention include 0.001 wt. % to 6 wt. % Spilanthes, 0.01 wt. % to 4 wt. % Spilanthes, or 0.05 wt. % to 2 wt. % Spilanthes, for example about 1.25 wt. % Spilanthes, 1.5 wt. % Spilanthes or 2 wt. % Spilanthes. Embodiments of the invention include 0.05 wt. % to 2 wt. % Spilanthes. Spilanthes may be a powder. Other suitable transdermal carriers may be used and they may be an oil, butter, or a powder.

Embodiments of the invention may also include one or more beneficial ingredients such as hormones, herbal roots and oils, amino acids, and dietary supplements. The personal care products of the present invention are particularly advantageous in that they can provide transdermal delivery of the one or more beneficial ingredients. Transdermal delivery can be further is promoted by the incorporation of argan oil, oleic acid, sucrose cocoate, spilanthes, peppermint extract, eucalyptus oil, niaouli oils, and other natural ingredients with transdermal properties.

Embodiments of the invention may include hormones selected from the group consisting of melatonin, progesterone/progestin, estrogen (estradiol, estrone, estriol), testosterone, oxytocin, insulin, prolactin, thyroxine, growth hormone, and vasopressin. Hormones used in the invention are generally obtained from nature or are synthetic hormones that are identical to natural hormones.

Embodiments of the invention may include herbal roots and oils selected from the group consisting of hemp oil, chamomile oil, valerian root, lavender, Ginkgo biloba, Ginkgo biloba nut extra, Ginkgo biloba leaf extract, chamomile oil, chamomile recutita flower, jasmium officinale flower extract, PEA N-palmitoyl-ethanolamine, spilanthes, spilanthes acmella flower extract, borage oil, quercetin, carnic acid, kojic acid, marshmallow root, nobiletin, menthol, capsaicin, comfrey, vitex, collagen, biotin, dong quai, and cystisine.

Embodiments of the invention may include amino acids selected from the group consisting of glucosamine-N Acetyl, carnosine, acetyl carnitine, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

Dietary supplements include vitamins, minerals and naturally occurring compounds that have beneficial effects in maintaining or improving health. Embodiments of the invention may include dietary supplements selected from the group consisting of Acai, Aloe Vera, Anabolic Steroids, Astragalus, Vitamin A, Bilberry, Biotin, Bitter Orange, Black Cohosh, Bromelain, Butterbur, Vitamin B1, Vitamin B3, Vitamin B12, Vitamin B2, Vitamin B6, Caffeine, Calcium, Carnitine, Cartilage (Bovine and Shark), Cat's Claw, Chamomile, Chasteberry, Chitosan, Choline, Chondroitin, Chromium, Cinnamon, Coenzyme Q10, Coleus forskohlii (forskolin), Colloidal Silver, Conjugated linoleic acid, Copper, Cranberry, Vitamin C, Dandelion, Vitamin D, Echinacea, Ephedra, Essiac/Flor-Essence, European Elder, Evening Primrose Oil, Vitamin E, Fenugreek, Feverfew, Fish Oil, Flaxseed, Fluoride, Folate, Fucoxanthin, Garcinia cambogia (hydroxycitric acid), Garlic, Ginger, Ginkgo, Ginseng, Glucomannan, Glucosamine, Goldenseal, Grape Seed Extract, Green coffee bean extract, Green Tea, Guar gum, Guarana, Hawthorn, Herbal Dietary Supplements, Hoodia, Horse Chestnut, Iodine, Iron, Kava, Kola nut (or cola nut), Vitamin K, Lavender, Licorice Root, Magnesium, Magnesium chloride, Melatonin, Milk Thistle, Mistletoe, Multivitamin/mineral Supplements, Niacin, Noni, Omega-3 Fatty Acids, Pantothenic Acid, PC-SPES, Peppermint Oil, Phosphorus, Pomegranate, Potassium, Pyruvate, Raspberry ketone, Red Clover, Riboflavin, Rhodiola, Sage, SAMe (S-Adenosyl-L-Methionine), Saw Palmetto, Selenium, Soy, St. John's Wort, Thiamin, Thunder God Vine, Turmeric, Valerian, White kidney bean (*Phaseolus vulgaris*), Yerba mate, Yohimbe, and Zinc.

Embodiments of the invention may include one or more ingredients selected from the group consisting of Ashwagandha, Arnica oil, Myrrh, Vitamin C, menthol crystals, Marshmallow root, Rose distillate, Essential oils, Menthol, and Carnosine.

The combination of ingredients, in particular the combination of plant butters and hyaluronic acid or a cannabis oil, are selected to achieve a pH comparable to that of skin, for example in the range of about 4-6. In preferred embodiments, the personal care products of the invention provide a pH of about 5.5 when applied to the skin in order to contribute to and maintain the optimal skin pH.

Embodiments of the invention may include sea buckthorn powder or extract of sea buckthorn (Hippophae). In some embodiments, sea buckthorn oil extracted from sea buckthorn berries may be used. Sea buckthorn oil, either taken orally or applied topically, is believed to be a skin softener. It has also been reported that sea buckthorn oil is effective for alleviating dry mucous membranes, such as eyes and mouth. Furthermore, sea buckthorn powder contains omega-7 fatty acid and when dissolved in a mixture, it generates an acidic pH in the mixture. A user suffering from bacterial vaginosis, trichomoniasis, and atrophic vaginitis generally has a vaginal pH of 4.5 or higher. The acidic nature of the sea buckthorn may restore the pH level of the vaginal area to a pH of 3.8 to 4.5, thus creating an environment where the vaginal flora may be restored. Embodiments of the invention include 0.0001 wt. % to 1 wt. % sea buckthorn powder, 0.005 wt. % to 0.5 wt. % sea buckthorn powder, or 0.05 wt. % to 0.15 wt. % sea buckthorn powder. Some embodiments of the invention include 0.05 wt. % to 0.15 wt. % sea buckthorn powder.

Embodiments of the invention include Vitamin E. Vitamin E is a natural preservative, which protects lipids and prevents the oxidation of polyunsaturated fatty acids. Embodiments of the invention include 0.1 wt. % to 10 wt. % Vitamin E, 1 wt. % to 8 wt. % Vitamin E, or 3 wt. % to 5 wt. % Vitamin E. Some embodiments of the invention include 3 wt. % to 5 wt. % Vitamin E. Other natural preservatives may also be used.

Embodiments of the invention may include menthol. Natural menthol may be extracted from corn mint, peppermint, or other mint oil. Menthol may be used to provide a cooling sensation on the skin. Other skin cooling oils may also be used. Embodiments of the invention include 0.5 wt. % to 3 wt. % menthol, 0.1 wt. % to 3 wt. % menthol, or 0.05 wt. % to 2 wt. % menthol. Some embodiments of the invention include 1 wt. % to 1.5 wt. % menthol.

Some embodiments of the invention may include witch hazel powder or extract (*Hammamelis Virginiana*) as a substitute for hyaluronic acid. Witch hazel powder is from flowering plants in the family of Hamamelidaceae. Witch hazel is a strong anti-oxidant and astringent. Embodiments of the invention include 0.0001 wt. % to 1 wt. % witch hazel (*Hammamelis Virginiana*), 0.005 wt. % to 0.5 wt. % witch hazel, or 0.05 wt. % to 0.15 wt. % witch hazel. Preferably, embodiments of the invention include 0.05 wt. % to 0.15 wt. % witch hazel (*Hammamelis Virginiana*). Witch hazel may be a powder or an oil.

Another embodiment of the invention relates to a personal care product that includes a natural fragrance, in particular, natural fragrances that provide a soothing effect by adding an aromatherapy aspect to the formulation. Natural fragrances include, for example, lavender oil and citrus extracts. Embodiments of the invention include 0.5 wt. % to 5 wt. % natural fragrance oil, 0.1 wt. % to 3 wt. % natural fragrance oil, or 0.05 wt. % to 1.5 wt. % natural fragrance oil. Some embodiments of the invention include 0.05 wt. % to 0.15 wt. % natural fragrance oil. The natural fragrance oil may be selected from the group consisting of lavender oil, sandalwood oil, jasmine oil, vanilla oil, gardenia oil, rose oil, and citrus oil. In particular, personal care products of the invention in the form of suppositories contain a natural fragrance oil.

The following manufacturing procedure may be used to manufacture personal care products according to the invention that are in the form of a cream.

Argan oil and oleic acid are combined and heated to 70° C. Powdered ingredients (for example, gingko, chasteberry, dong quai, valerian root, melatonin, spilanthes, etc.) are stirred in slowly. Plant-based glycerides (for example, cocoa butter, kokum butter, rhea olein) are added and heated and stirred at 70° C. for between 30 minutes to 1 hour. Other ingredients, such as fragrance or menthol may also be added to the mixture. The mixture is stirred for at elevated temperature or until homogeneous. Any large particles may be filtered out. The product may be filled into final dispenser and cool to -4° C. The product may be stored at room temperature.

Embodiments of the invention relate to using pharmaceutical grade ingredients, manufacturing under good manufacturing practice, and testing final product for levels of heavy metals below 0.1 ppm, yeast and mold less than 10 cfu/g, and negative detection for *E. coli*, Salmonella, Staphylococcus aureus and Pseudomonas aeruginosa.

EXAMPLES

Examples of hyaluronic acid containing formulations are provided below. In any of the examples, hyaluronic acid may be replaced by a cannabis oil.

Example 1—Face Cream

A face cream formulation for alleviating dryness that can also serve as a sleep aid can be formulated as follows:

| Ingredient | Possible Range (wt. %) | Exemplary Range (wt. %) |
| --- | --- | --- |
| Cocoa Butter | 3-10 | 5-8 |
| Kokum Butter | 3-10 | 3-5 |
| Vitamin E | 0.2-3 | 0.5-1.5 |
| Hyaluronic acid (Sodium Hyaluronate) | 0.01-2 | 0.05-0.5 |
| Shea olein | 6-15 | 10-14 |
| Oleic Acid Glycerides | 30-40 | 33-38 |
| Argan Oil | 0.5-5 | 1-3 |
| Magnesium | 0.01-2 | 0.5-1 |
| Hemp Oil | 25-35 | 28-33 |
| Borage Oil | 3-10 | 4-7 |
| Vitamin D3 | 0.01-2 | 0.05-1 |
| Chamomile Oil | 0.01-2 | 0.05-1 |
| Valerian Root | 0.01-2 | 0.05-1 |
| Lavender | 0.01-2 | 0.05-1 |
| Total | 100 | 100 |

Example 2—Face Cream with Sleep Aid

A face cream formulation for alleviating dryness that can also serve as a sleep aid can be formulated as follows:

| Ingredient | Possible Range (wt. %) | Exemplary Range (wt. %) |
| --- | --- | --- |
| Cocoa Butter | 3-10 | 5-8 |
| Kokum Butter | 3-10 | 3-5 |
| Vitamin E | 0.2-3 | 0.5-1.5 |

-continued

| Ingredient | Possible Range (wt. %) | Exemplary Range (wt. %) |
|---|---|---|
| Hyaluronic acid (Sodium Hyaluronate) | 0.01-2 | 0.05-0.5 |
| Shea olein | 6-15 | 10-14 |
| Oleic Acid Glycerides | 30-40 | 33-38 |
| Argan Oil | 0.5-5 | 1-3 |
| Magnesium | 0.01-2 | 0.5-1 |
| Hemp Oil | 25-35 | 28-33 |
| Borage Oil | 3-10 | 4-7 |
| Vitamin D3 | 0.01-2 | 0.05-1 |
| Chamomile Oil | 0.01-2 | 0.05-1 |
| Valerian Root | 0.01-2 | 0.05-1 |
| Lavender | 0.01-2 | 0.05-1 |
| Melatonin | 0.05-4 | 0.1-2 |
| Sodium Cocoate | 0.5-6 | 1-4 |
| Total | 100 | 100 |

Example 3—Breast Cream

A breast cream formulation for alleviating dryness and soothing pain and discomfort can be formulated as follows:

| Ingredient | Possible Range (wt. %) | Exemplary Range (wt. %) |
|---|---|---|
| Cocoa Butter | 3-10 | 5-8 |
| Kokum Butter | 3-10 | 3-5 |
| Vitamin E | 0.2-3 | 0.5-1.5 |
| Hyaluronic acid (Sodium Hyaluronate) | 0.01-2 | 0.05-0.5 |
| Shea olein | 6-15 | 10-14 |
| Oleic Acid Glycerides | 30-40 | 33-38 |
| Argan Oil | 0.5-5 | 1-3 |
| Magnesium | 0.01-2 | 0.5-1 |
| Hemp Oil | 25-35 | 28-33 |
| Borage Oil | 3-10 | 4-7 |
| Spilantes | 0.01-4 | 0.5-3 |
| Chasteberry | 0.01-2 | 0.05-1 |
| Dong Quai | 0.01-2 | 0.05-1 |
| Maca | 0.01-2 | 0.05-1 |
| Black cohash | 0.01-2 | 0.05-1 |
| Total | 100 | 100 |

Example 4—Smoothing Facial Serum

A facial serum formulation can be formulated as follows:

| Ingredient | Possible Range (wt. %) | Exemplary Range (wt. %) |
|---|---|---|
| Cocoa Butter | 1-7 | 2-5 |
| Shea olein | 6-15 | 7-11 |
| Kokum Butter | 0.1-5 | 0.5-3 |
| Vitamin E | 0.2-3 | 0.5-1.5 |
| Oleic Acid Glycerides (Sunflower oil) | 30-40 | 33-38 |
| Argan Oil | 9-15 | 10-15 |
| Borage Oil | 3-10 | 4-7 |
| Hemp Oil | 25-35 | 28-33 |
| Hyaluronic acid (Sodium Hyaluronate) | 0.01-2 | 0.05-0.5 |
| Magnesium (MgCl) | 0.01-2 | 0.05-1 |
| Chamomile Oil | 0.01-2 | 0.05-1 |
| Sucrose Cocoate | 0.5-6 | 1-4 |
| Vitamin D3 | 0.01-2 | 0.05-1 |
| Rose Oil | 0.01-2 | 0.05-1 |
| Gingko Biloba extract | 0.01-2 | 0.05-1 |
| Cannabis Oil | 0.01-2 | 0.05-1 |
| Total | 100 | 100 |

Example 5—Luminizing Facial Serum

A luminizing or brightening facial serum formulation can be formulated as follows:

| Ingredient | Possible Range (wt. %) | Exemplary Range (wt. %) |
|---|---|---|
| Cocoa Butter | 1-7 | 2-5 |
| Shea olein | 6-15 | 7-11 |
| Kokum Butter | 0.1-5 | 0.5-3 |
| Vitamin E | 0.2-3 | 0.5-1.5 |
| Hyaluronic acid (Sodium Hyaluronate) | 0.01-2 | 0.05-0.5 |
| Oleic Acid Glycerides (Sunflower oil) | 30-40 | 33-38 |
| Argan Oil | 9-15 | 10-15 |
| Borage Oil | 3-10 | 4-7 |
| Hemp Oil | 25-35 | 28-33 |
| Kojic acid | 0.01-2 | 0.05-1 |
| Glucosamine | 0.1-5 | 0.5-5 |
| Rose Oil | 0.01-2 | 0.03-1 |
| Sucrose Cocoate | 0.5-6 | 1-4 |
| Cannabis Oil | 0.01-2 | 0.05-1 |
| Lavendar | 0.01-2 | 0.05-1 |
| Total | 100 | 100 |

Example 6—Massage Oil

A massage oil formulation can be formulated as follows:

| Ingredient | Possible Range (wt. %) | Exemplary Range (wt. %) |
|---|---|---|
| Cocoa Butter | 1-7 | 2-5 |
| Kokum Butter | 0.1-5 | 0.5-3 |
| Vitamin E | 0.2-3 | 0.5-1.5 |
| Shea olein | 6-15 | 7-12 |
| Oleic Acid Glycerides (Sunflower Oil) | 30-40 | 30-38 |
| Argan Oil | 9-15 | 10-15 |
| Hemp Oil | 25-35 | 28-33 |
| Borage Oil | 3-10 | 4-7 |
| Sucrose Cocoate | 0.01-4 | 0.5-3 |
| Cannabis Oil | 0.01-2 | 0.05-1 |
| Lemongrass extract | 0.01-2 | 0.05-1 |
| Total | 100 | 100 |

Example 7—Sleep Cream Clinical Study

A clinical study was conducted using the face cream with sleep aid of Example 2 on three individuals. To measure the skin permeation capabilities of the composition, the sleep aid of example 1 was prepared with varying concentrations of melatonin, as shown in the Dose column below. After application of the lotion to the skin, melatonin content in the bloodstream was measured at various time points. The results shown below demonstrate that the formulations of the invention promote transdermal delivery of contained melatonin and several different concentrations

| Sample ID | Rep 1 | Rep 2 | Mean (pg/mL) | Subject | Dose | Timepoint |
|---|---|---|---|---|---|---|
| 6 | 49.22 | 46.90 | 48.06 | A | 0 | Pre Dose |
| 7 | 72.55 | 60.69 | 66.62 | A | 0 | Pre Dose |
| 8 | 87.45 | 85.50 | 86.47 | A | 0 | Pre Dose |
| 9 | >500.00 | >500.00 | >500.00 | A | 5 mg in 5 ml | 45 minutes |
| 10 | 147.82 | 140.42 | 144.12 | A | 5 mg in 5 ml | 9 hours |
| 11 | 258.31 | 254.74 | 256.52 | A | 5 mg in 5 ml | 15 hours |
| 12 | 187.13 | 197.02 | 192.07 | B | 12 mg in 3 ml | Pre Dose |
| 13 | 455.07 | 463.44 | 459.26 | B | 12 mg in 3 ml | 6 hours |
| 20 | 198.05 | 197.71 | 197.88 | A | 15 mg in 1 ml | Pre Dose |
| 21 | >500.00 | >500.00 | >500.00 | A | 15 mg in 1 ml | 8 hours |
| 22 | 191.98 | 195.66 | 193.82 | C | 15 mg in 1 ml | Pre Dose |
| 23 | >500.00 | >500.00 | >500.00 | C | 15 mg in 1 ml | 45 minutes |
| 24 | 191.00 | 192.98 | 191.99 | C | 15 mg in 1 ml | 12 hours |

While the present invention has been described as containing cocoa butter, kokum butter and shea olein, it will be appreciated that one or more of these specific glycerides may be replaced by a plant glyceride of different origin. If a different plant glyceride is used, it should have similar physical properties, in particular, similar consistency and behavior, and provide additional properties consistent with the teachings of this specification.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever.

We claim:

1. A personal care product, comprising:
   about 1 wt. % to about 10 wt. % cocoa butter;
   about 0.1 wt. % to about 10 wt. % kokum butter;
   about 6 wt. % to about 15 wt. % shea olein;
   less than 5% added water;
   about 0.01 wt. % to about 2 wt. % hyaluronic acid or about 0.01 wt. % to about 2 wt. % cannabis oil, or a combination thereof;
   about 30 wt. % to about 40 wt. % oleic acid glyceride;
   about 25 wt. % to about 35 wt. % hemp oil;
   about 9 wt. % to about 15 wt. % argan oil; and
   about 3 wt. % to about 10 wt. % borage oil;
   wherein the cocoa butter, kokum butter, and shea olein are deodorized.

2. The personal care product of claim 1, comprising:
   about 1 wt. % to about 7 wt. % cocoa butter;
   about 0.1 wt. % to about 5 wt. % kokum butter.

3. The personal care product of claim 1, comprising:
   about 2 wt. % to about 5 wt. % cocoa butter;
   about 0.5 wt. % to about 3 wt. % kokum butter;
   about 7 wt. % to about 11 wt. % shea olein; and
   about 0.05 wt. % to about 0.5 wt. % hyaluronic acid, 0.05 wt. % to about 1 wt. % cannabis oil, or a combination thereof.

4. The personal care product of claim 1, further comprising one or more of an oleic acid glyceride, argan oil, or hemp oil.

5. The personal care product of claim 1, comprising:
   about 33 wt. % to about 38 wt. % oleic acid glyceride;
   about 28 wt. % to about 33 wt. % hemp oil; and
   about 4 wt. % to about 7 wt. % borage oil.

6. The personal care product of claim 1, wherein the cannabis oil comprises one or more of, THC (Tetrahydrocannabinol), THCA (Tetrahydrocannabinolic acid), CBD (Cannabidiol), CBDA (Cannabidiolic Acid), CBN (Cannabinol), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), CBE (Cannabielsoin), and CBT (Cannabicitran).

7. The personal care product of claim 6, wherein at least 65 wt. % of the cannabinoid content comprises decarboxylated CBD.

8. The personal care product of claim 1, further comprising about 1 wt. % to about 3 wt. % THC.

9. The personal care product of claim 1, comprising:
   about 1 wt. % to about 7 wt. % cocoa butter;
   about 0.1 wt. % to about 5 wt. % kokum butter;
   about 6 wt. % to about 15 wt. % shea olein;
   about 0.01 wt. % to about 2 wt. % cannabis oil;
   about 30 wt. % to about 40 wt. % oleic acid glyceride;
   about 25 wt. % to about 35 wt. % hemp oil;
   about 3 wt. % to about 10 wt. % borage oil;
   about 9 wt. % to about 15 wt. % argan oil; and
   sucrose cocoate.

10. The personal care product of claim 9, further comprising about 0.01 wt. % to about 2 wt. % hyaluronic acid.

11. The personal care product of claim 9, comprising:
    about 2 wt. % to about 5 wt. % cocoa butter;
    about 0.5 wt. % to about 3 wt. % kokum butter;
    about 7 wt. % to about 11 wt. % shea olein;
    about 0.05 wt. % to about 1 wt. % cannabis oil;
    about 33 wt. % to about 38 wt. % oleic acid glyceride;
    about 28 wt. % to about 33 wt. % hemp oil;
    about 4 wt. % to about 7 wt. % borage oil; and
    about 10 wt. % to about 15 wt. % argan oil.

12. The personal care product of claim 11, further comprising about 0.01 wt. % to about 0.5 wt. % hyaluronic acid.

13. The personal care product of claim 9, further comprising Vitamin E, Vitamin D3, chamomile oil, magnesium chloride, and Ginkgo biloba extract.

14. The personal care product of claim 9, comprising 0.01-6 wt. % sucrose cocoate.

15. The personal care product of claim 9, further comprising Vitamin E, glucosamine, kojic acid, and lavender.

16. The personal care product of claim 1, wherein the personal care product is substantially free of added water or alcohol.

17. The personal care product of claim 1, wherein the personal care product is in a form of a serum or an oil.

18. The personal care product of claim 9, further comprising vitamin E and lemongrass extract.

19. The personal care product of claim 9, comprising 0.01-4 wt. % sucrose cocoate.

* * * * *